United States Patent
Mitchell

Patent Number: 5,387,420
Date of Patent: Feb. 7, 1995

[54] MORPHINE-CONTAINING EFFERVERSCENT COMPOSITION

[75] Inventor: Robin P. Mitchell, Brussels, Belgium

[73] Assignee: May & Baker Ltd., Essex, England

[21] Appl. No.: 2,514

[22] Filed: Jan. 8, 1993

Related U.S. Application Data

[63] Continuation of Ser. No. 758,702, Sep. 9, 1991, abandoned, which is a continuation of Ser. No. 398,940, Aug. 28, 1989, abandoned.

[30] Foreign Application Priority Data

Aug. 26, 1988 [GB] United Kingdom ............... 8820327

[51] Int. Cl.⁶ .................................................. A61K 9/46
[52] U.S. Cl. .................................. 424/466; 424/443; 424/473
[58] Field of Search .................. 424/466, 473, 443

[56] References Cited

U.S. PATENT DOCUMENTS

| | | | |
|---|---|---|---|
| 2,211,485 | 8/1940 | Zimmenman | 424/466 |
| 3,136,692 | 6/1964 | Bandelin | 424/80 |
| 4,235,236 | 11/1980 | Theeuwes | 424/473 |
| 4,332,789 | 6/1982 | Mlodozeniec | 424/444 |
| 4,806,358 | 2/1989 | Khan et al. | 424/466 |
| 4,911,930 | 3/1990 | Gergely et al. | 424/466 |

Primary Examiner—Thurman K. Page
Assistant Examiner—William E. Benston, Jr.
Attorney, Agent, or Firm—Morgan & Finnegan

[57] ABSTRACT

In an effervescent formulation containing morphine, inclusion of the morphine in the basic component gives superior storage stability.

7 Claims, No Drawings

MORPHINE-CONTAINING EFFERVERSCENT COMPOSITION

This is a continuation of co-pending application Ser. No. 07/758,702, filed on Sep. 9, 1991, now abandoned, which is co-pending of application Ser. No. 07/398,940, filed Aug. 28, 1989, now abandoned.

FIELD OF THE INVENTION

This invention relates to a novel pharmaceutical formulation and a process for its preparation.

BACKGROUND OF THE INVENTION

Effervescent formulations are a particularly acceptable way of presenting many drugs to patients, especially if they need to be taken on a long term or regular basis.

Effervescence is the evolution of bubbles from a liquid, for example as a result of chemical action. In the case of pharmaceutical products this gas is normally carbon dioxide which is liberated by the reaction between a physiologically acceptable acid (e.g. citric, tartaric or malic acid) and a source of carbonate (such as sodium carbonate, sodium bicarbonate or a mixture thereof). It is convenient for these basic and acidic components of the "effervescent couple" to be separately granulated (e.g. by wet granulation, preferably in water), dried and then combined prior to or during packaging. The resultant mixture will then produce effervescence on being added to water.

Morphine is a drug which is often taken on a long term or regular basis and although it is available in a number of forms it has so far not been produced in an effervescent formulation.

It is known that morphine is normally degraded by oxidation, promoted by a wide variety of circumstances, and that this occurs more readily in basic media. It would therefore appear obvious to incorporate the morphine into the acid component of the effervescent couple. A further advantage would appear to be that ascorbic acid could be incorporated in this acidic mixture as an antioxidant. When such a composition is made up however, it is found that a significant decrease in activity occurs during storage. Analysis shows that this is due to esterification of phenolic groups in the morphine by the acids.

DESCRIPTION OF THE INVENTION

It has surprisingly been found that incorporation of the morphine in the basic component of an effervescent couple does not lead to any substantial loss in activity, even when it is in contact with granules of the acidic component.

Thus the invention provides a granule for inclusion in an effervescent formulation comprising morphine or a pharmaceutically acceptable salt thereof and the basic component of an effervescent couple.

The basic component is preferably sodium carbonate, sodium bicarbonate or a mixture thereof.

The invention also provides an effervescent formulation comprising such granules.

The morphine is generally present in the form of a pharmaceutically acceptable salt, for example morphine hydrochloride or morphine sulphate.

The stability of the effervescent morphine formulation according to the invention allows it to be readily incorporated into unit dosage forms, especially sachets. These typically contain 5, 10 or 30 mg of morphine sulphate and dissolution of the contents of one or two of them in water allows a number of doses of from 5 to 60 mg—or more if required—to be conveniently prepared and taken.

Granules containing the basic component of the couple are typically prepared by dry mixing morphine sulphate, sodium bicarbonate and a solid binder material such as polyvinylpyrrolidone (PVP), granulation in an aqueous solution of binder (again typically PVP in a concentration of for example 20% w/w), drying and milling. The PVP used can be for example PVP K30. Granulation may be performed in a high speed granulator (e.g. a Fielder or Diosna granulator), drying in a fluid bed drier (e.g. as manufactured by Glatt or Aeromatic) or an oven, typically at 60° C., and milling on a 2 mm screen (e.g. Glatt Quicksieve).

The relative amounts of solid and aqueous binder (PVP) depend—as normal in granulation processes—on the scale of the process and can be easily determined by those skilled in the art.

Acidic granules can be prepared in a similar fashion starting from, for example, tartaric acid and/or citric acid and binder (PVP) and can also include ascorbic acid.

The final product can then be obtained by mixing these two granular materials with extragranular components such as sodium carbonate, sweeteners (e.g. aspartame) and flavorings (e.g. Lemon Juice Flav-O-Lok). This can be carried out in a blender, such as an Oblicone cone blender, a Turbula mixer or a Flow-bin type blender.

EXAMPLES

The following Examples illustrate the invention:

EXAMPLE 1

Basic granules were formed by dry-mixing morphine sulphate B.P. (17.5 g) sodium bicarbonate B.P. (2813 g) and solid PVP, granulating with an aqueous solution of PVP (PVP K30, total weight of PVP used 63.7 g), drying at 60° C. and passing through a 2 mm screen.

Acidic granules were prepared in a similar manner using tartaric acid B.P. (2013 g), anhydrous citric acid B.P. (1224 g) and solid and aqueous PVP (total weight 30.1 g).

The two batches of granules were then mixed together along with sodium carbonate BPC (703.5 g), aspartame ('Nutrasweet', 105 g) and 'Lemon Juice Flav-O-Lok 610406E' flavoring (28 g), to produce a product having the following overall composition (w/w/):

| | |
|---|---|
| Morphine sulphate | 0.25% |
| PVP | 1.35% |
| Sodium bicarbonate | 40.2% |
| Tartaric acid | 28.75% |
| Citric acid | 17.5% |
| Sodium carbonate | 10.05% |
| Aspartame | 1.5% |
| Flav-O-Lok | 0.4% |

This was then filled into sachets, each of which nominally contained 5 mg of morphine sulphate (total sachet contents approximately 2 g)

EXAMPLES 2 AND 3

Sachets nominally containing 10 and 30 mg of morphine sulphate in a total weight of 2 g were prepared in a similar manner—the appropriate weight of sodium bicarbonate being replaced by morphine sulphate in the initial basic mix.

REFERENCE EXAMPLE

An unsatisfactory (unstable) composition was prepared in a similar manner by mixing acidic granules made from morphine sulphate (17.5 g), citric acid (1224 g), tartaric acid (2010 g) and PVP (30.2 g) and basic granules made from sodium bicarbonate (2813 g) and PVP (64.3 g) with sodium carbonate (703.5 g), aspartame (105.5 g) and Flav-o-Lok (28.1 g).

The relative stability of the formulation according to the invention is shown in Table I. Samples were prepared in a similar manner to those in Example 1 and the Reference Example above.

TABLE I

| | morphine sulphate content (mg/sachet) | |
|---|---|---|
| Conditions | morphine in acidic granules | morphine in basic granules |
| Initial | 4.97 | 5.04 |
| one month at:- | | |
| room temperature | 4.69 (94.4%) | |
| 22° C./55% r.h.* | | 4.93 (97.8%) |
| 37° C./80% r.h. | 4.52 (90.9%) | 4.95 (98.2%) |
| 45° C./ambient humidity | 4.04 (81.3%) | 4.87 (96.6%) |

*r.h. = relative humidity

Similar samples with morphine in the basic granules were also tested as shown in Table II.

TABLE II

| | % morphine still present after | | |
|---|---|---|---|
| test conditions | 3 months | 6 months | 12 months |
| 22° C./55% r.h. | 98.4 | 97.4 | 95.6 |
| 37° C./ambient humidity | 96.0 | 95.4 | 92.7 |
| 37° C./80% r.h. | 100.0 | 98.2 | 94.6 |
| 45° C./ambient humidity | 94.8 | 96.0 | not tested |

Samples containing 30 mg morphine sulphate in the basic granules showed no significant loss in active material content under any of the conditions listed above.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. An effervescent morphine-containing composition comprising a mixture of discrete stable morphine-containing basic granules and discrete acidic granules in physical contact with one another, said discrete morphine-containing basic granules comprising morphine or a pharmaceutically acceptable salt thereof bound in admixture with a source of carbonate, and said discrete acid granules containing a physiologically acceptable acid that reacts with said source of carbonate in the presence of water to release carbon dioxide.

2. A granule according to claim 1 which comprises a solid binder material.

3. A granule according to claim 2, wherein the solid binder material is polyvinylpyrrolidone.

4. A granule according to claim 1 in which the morphine is present as morphine sulphate.

5. The composition of claim 2 in which the acidic granules comprise a binder and an acid selected from the group consisting of tartaric, citric acid and mixtures thereof.

6. An effervescent morphine-containing formulation comprising a mixture of (a) discrete stable basic granules which include morphine sulphate and a basic component selected from the group consisting of sodium carbonate, sodium bicarbonate and mixtures thereof, and a solid binder material; and (b) discrete acidic granules in physical contact with said basic granules and including an acidic component selected from the group consisting of tartaric acid, citric acid and mixtures thereof, and a binder; whereby the acid component reacts with the basic component in the presence of water to release carbon dioxide.

7. The composition of claim 1 wherein said source of carbonate is selected from the group consisting of sodium carbonate, sodium bicarbonate and mixtures thereof.

* * * * *